United States Patent [19]

Czuba et al.

[11] 3,991,053

[45] Nov. 9, 1976

[54] ANTIBACTERIAL 1,3-DIHYDROFURO[3,4-B]QUINOXALINE 4,9-DIOXIDES

[75] Inventors: Leonard J. Czuba, Stonington; John P. Dirlam, Gales Ferry, both of Conn.

[73] Assignee: Pfizer Inc., New York, N.Y.

[22] Filed: Aug. 6, 1975

[21] Appl. No.: 602,514

[52] U.S. Cl. .................. 260/250 QN; 260/345.9; 424/250
[51] Int. Cl.² ................................ C07D 491/04
[58] Field of Search ............... 260/250 Q, 250 QN

[56] References Cited
UNITED STATES PATENTS
3,344,022 9/1967 Johnston ................. 260/250 QN

OTHER PUBLICATIONS

Edwards et al., J. Med. Chem. 18, 637 (1975).

Elena et al., Chem. Abs. 71, 13093y (1969).

Primary Examiner—Alton D. Rollins
Assistant Examiner—Mark L. Berch
Attorney, Agent, or Firm—Connolly and Hutz

[57] ABSTRACT

Novel 1-substituted 1,3-dihydrofuro[3,4-b]quinoxaline 4,9-dioxides are useful as antimicrobial agents, and as agents for promoting growth and feed efficiency in animals.

3 Claims, No Drawings

3,991,053

ANTIBACTERIAL 1,3-DIHYDROFURO[3,4-B]QUINOXALINE 4,9-DIOXIDES

BACKGROUND OF THE INVENTION

U.S. Pat. No. 3,344,022 discloses a wide variety of substituted quinoxaline 1,4-dioxide compounds. One particular structural type included within the broad genus of compounds disclosed is quinoxaline 1,4-dioxides with an acetyl group at the 2-position and a hydroxymethyl group at the 3-position. However, the said United States patent does not specifically identify any quinoxaline 1,4-dioxides with a 2-acetyl group and a 3-hydroxymethyl group, and it does not specifically teach how to make such compounds. In attempting to prepare 2-acetyl-3-hydroxymethylquinoxaline 1,4-dioxide by standard procedures, it has now been found that the products obtained are 1,3-dihydrofuro[3,4-b]quinoxaline, 4,9-dioxides of the formula

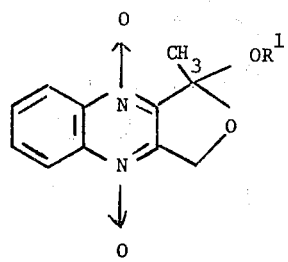

wherein $R^1$ is hydrogen, or a moiety derived from the solvent ($R^1OH$) in which the reaction is run when said solvent is an alcohol.

Edwards, Bambury and Ritter, in the *Journal of Medicinal Chemistry*, 18, 637 (1975), describe the preparation and antibacterial activity of 1-hydroxy-1,3-dihydrofuro[3,4-b]quinoxaline 4,9-dioxide.

The compounds of the instant invention are derivatives of 1,3-dihydrofuro[3,4-b]quinoxaline 4,9-dioxide, and they are useful as antimicrobial agents for prophylaxis and therapy of economically important diseases in farm animals, and for the promotion of growth in farm animals.

SUMMARY OF THE INVENTION

It is an object of this invention to provide novel compounds of the formula

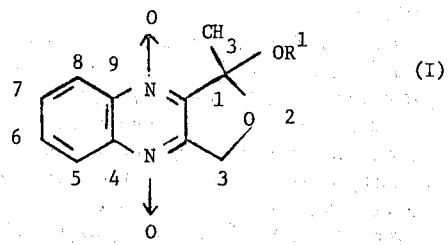

wherein $R^1$ is selected from the group consisting of hydrogen, alkyl having from one to six carbon atoms and benzyl, said compounds being valuable as antimicrobial agents and as agents for the promotion of growth in animals. The preferred compounds of the invention are the compound of formula I, wherein $R^1$ is hydrogen, and the compound of formula I, wherein $R^1$ is methyl.

DETAILED DESCRIPTION OF THE INVENTION

As indicated hereinbefore, it is an object of this invention to provide novel antimicrobial agents of the formula I, wherein $R^1$ is selected from the group consisting of hydrogen, alkyl having from one to six carbon atoms and benzyl.

In one method, according to the invention, the compound of formula I, wherein $R^1$ is hydrogen, is prepared by hydrolysis of the compound of formula

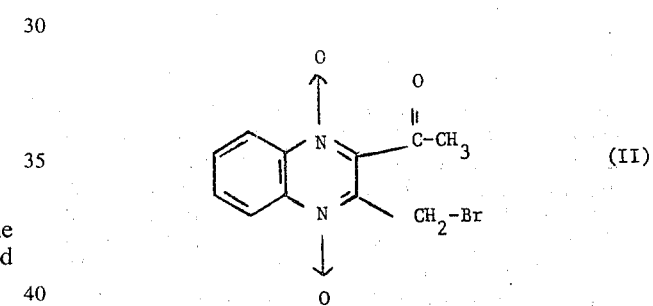

Thus, the compound of formula II is treated with water. Although use of as low as about five molar equivalents of water, based on bromo compound, will successfully lead to the formation of the compound of formula I, wherein $R^1$ is hydrogen, it is common to use a large excess of water. Indeed it is common to use a sufficient amount of water that it is not necessary to use another reaction solvent. However, a co-solvent which is miscible with water, which will dissolve the compound of formula II, and which does not adversely interact with either the starting material or the final product can be used. Examples of such solvents are ethers, such as tetrahydrofuran, dioxan and 1,2-dimethoxyethane, and amides, such as N,N-dimethylformamide and N-methylpyrrolidone. The hydrolysis reaction is normally carried out at a temperature in the range from about 50° C. to 150° C., and preferably at about 100° C. At about 100° C. the reaction takes several hours, e.g. about 12 hours, to proceed substantially to completion. As will be appreciated by one skilled in the art, the reaction proceeds more quickly at higher temperatures and more slowly at lower temperatures. The reaction product is recovered by standard methods. If the product is out of solution at the end of the reaction, it can be recovered by filtration. Alternatively, if the product remains dissolved at the end of the reaction, it can be recovered by evaporation, or by solvent extraction, according to standard procedures.

In another method, according to the invention, the compound of formula I, wherein $R^1$ is hydrogen, is prepared by an acid-catalysed hydrolysis of a compound of formula

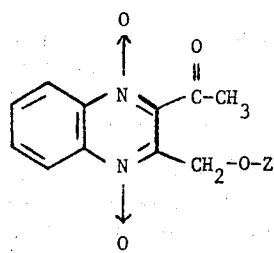

(III)

wherein Z represents the acyl moiety of an organic carboxylic acid. A wide variety of acyl groups can serve as Z, such as formyl, alkanoyl, halogen-substituted alkanoyl, alkoxy-substituted alkanoyl, aroyl, substituted aroyl, heteroaroyl, substituted heteroaroyl, and the like. However, particularly convenient Z groups are lower-alkanoyl, particularly acetyl, and benzoyl. The acid-catalysed hydrolysis of the said compound of formula III is usually carried out by contacting the starting material with an aqueous solution of a strong acid, at or about ambient temperature, for a time period of from about one hour to about twenty hours, and usually about four hours. Any acid with a $pK_a$ of less than about 2.5 can be used, but particularly convenient acids are hydrochloric acid, sulfuric acid and phosphoric acid. The concentration of the acid is normally in the range from about five-normal (5N) to about fifteen-normal (15N), and preferably about ten-normal (10N). It is desirable to use an excess, preferably at least about five molar equivalents, of water, and in most instances sufficient water to obviate the need for a further solvent is employed. However, co-solvents which do not adversely interact with either the starting material or the product, such as tetrahydrofuran or acetone, can be used, if desired. The product is isolated by standard procedures, such as solvent extraction.

In still another method, according to the invention, the compound of formula I, wherein $R^1$ is hydroxy, is prepared via condensation of benzofurazan 1-oxide with a 1-(protected hydroxy)-2,4-pentanedione, followed by removal of the protecting group. Appropriate protecting groups are those which are stable to the basic conditions under which the condensation between the benzofurazan 1-oxide and the 2,4-pentanedione derivative is carried out, and which can then be removed without degradation of the final product. A particularly convenient protecting group is the 2-tetrahydropyranyl group, since 1-(2-tetrahydropyranyloxy)-2,4-pentanedione readily condenses with benzofurazan 1-oxide, to give 2-acetyl-3-(2-tetrahydropyranyloxymethyl)-quinoxaline 1,4-dioxide, and then removal of the 2-tetrahydropyranyloxy group with dilute aqueous acid produces the compound of formula I, wherein $R^1$ is hydrogen, viz:

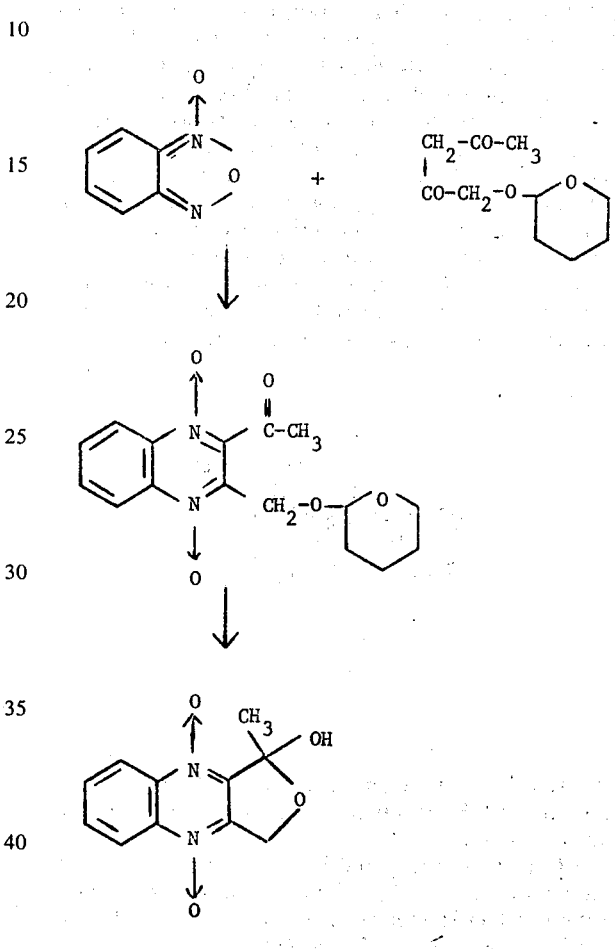

The condensation between the benzofurazan 1-oxide and the 1-(2-tetrahydropyranyloxy)-2,4-pentanedione is carried out using standard procedures, known for this type of reaction. See, for example, U.S. Pat. No. 3,660,398, and British patents Nos. 1,215,815 and 1,308,370. However, a particularly convenient method of carrying out this condensation reaction involves reacting the benzofurazan 1-oxide and the diketone in ethanol, at about ambient temperature, for several hours, in the presence of powdered sodium hydroxide as catalyst. Removal of the tetrahydropyranyl protecting group is also carried out using well-known procedures, for example, using aqueous acetic acid at about 40° C. for several hours.

In one method, according to the invention, the compounds of formula I, wherein $R^1$ is selected from the group consisting of alkyl having from one to six carbon atoms and benzyl, are prepared by a process which comprises treating a compound of formula III, wherein Z is as previously defined, with the appropriate alkanol having from one to six carbon atoms or benzyl alcohol in the presence of an acid catalyst. The reaction is normally carried out by contacting the compound of formula III with the appropriate alkanol or benzyl alcohol at a temperature in the range from about 0° C. to about 100° C., and preferably at about ambient temperature, in the presence of an acid catalyst. Any acid having a $pK_a$ less than about 2.5 can be used as the catalyst, and typical examples of acids which can be used are hydrogen chloride, hydrogen bromide, methanesulfonic acid, benzenesulfonic acid, p-toluenesulfonic acid, trifluoroacetic acid and trichloroacetic acid. Generally, the acid is present in an amount from about 0.01 to 1.0 molar equivalents, but amounts larger than one molar equivalent are sometimes used. It is desirable to use an excess, preferably at least five molar equivalents, of the alkanol, and in most instances sufficient alkanol is used to obviate the need for a further solvent. However, a further solvent which is miscible with the alkanol and does not adversely interact with either the starting material or the product can be added, if desired. Typical examples of such solvents include ether, tetrahydrofuran, dioxan, 1,2-dimethoxymethane, benzene, chloroform and methylene chloride. When working at about ambient temperature the reaction commonly takes from one to about five days to produce a satisfactory yield of product. The product is isolated by standard methods. For example, in those instances where the product precipitates during the course of the reaction, it can be recovered simply by filtration. Alternatively, when the product does not precipitate spontaneously, it can often be induced to precipitate at the end of the reaction by dilution of the reaction medium with a non-solvent, such as ether, hexane or water. A further method of product recovery involves removal of the solvents by evaporation, followed by partitioning of the crude product thus obtained between water and a water-immiscible organic solvent. After separation of the two phases, the product-containing phase is evaporated, to yield the product.

In another method, according to the invention, the compounds of formula I, wherein $R^1$ is selected from the group consisting of alkyl having from one to six carbon atoms and benzyl, are obtained by treating the compound of formula I, wherein $R^1$ is hydrogen, with the appropriate alkanol having from one to six carbon atoms or benzyl alcohol, in the presence of an acid catalyst. This reaction is carried out using the same acid catalysts and the same reaction conditions as described peviously for the conversion of a compound of formula III into a compound of formula I, wherein $R^1$ is the said alkyl or benzyl.

If desired, the compounds of formula I, wherein $R^1$ is the said alkyl or benzyl, can be converted into the compound of formula I, wherein $R^1$ is hydrogen. This transformation is achieved by an acid-catalysed hydrolysis reaction, and it can be carried out using the same acid catalysts and reaction conditions described previously for conversion of a compound of formula III into the compound of formula I, wherein $R^1$ is hydrogen. However, a particularly convenient method of converting a compound of formula I, wherein $R^1$ is the said alkyl or benzyl, into the compound of formula I, wherein $R^1$ is hydrogen, involves treating the starting material with aqueous acetone, under reflux, in the presence of about 0.1 molar equivalents of an organic sulfonic acid, e.g. 4-toluenesulfonic acid, for a few hours.

The 2-acetyl-3-acyloxymethylquinoxaline 1,4-dioxides of formula III, which are useful as starting materials for the compounds of the present invention, are prepared by reaction of the bromo compound of formula II with the potassium salt of the appropriate carboxylic acid. The reaction is usually carried out by reacting substantially equimolar proportions of the bromo compound and the carboxylate salt, at about ambient temperature, in a polar organic solvent such as N,N-dimethylformamide, for a few hours. The addition of potassium iodide can be used to speed up the reaction if desired.

The 2-acetyl-3-bromomethylquinoxaline 1,4-dioxide starting material is prepared by bromination of 2-acetyl-3-methylquinoxaline 1,4-dioxide. The bromination reaction is conveniently carried out by treating 2-acetyl-3-methylquinoxaline 1,4-dioxide with a slight excess of molecular bromine, in methanol, at ambient temperature, for a few days. Preparation of 2-acetyl-3-methylquinoxaline 1,4-dioxide is described in British Pat. No. 1,215,815.

The novel 1,3-dihydrofuro[3,4-b]quinoxaline 4,9-dioxide compounds of formula I, wherein $R^1$ is hydrogen, alkyl having from one to six carbon atoms or benzyl are useful as antimicrobial agents, and in particular they show valuable antibacterial activity both in vitro and in vivo.

The in vitro antibacterial activity of the compounds of the present invention can be demonstrated by the conventional two-fold serial dilution technique in Brain-Heart Infusion Broth (Difco). The broth is inoculated with bacteria, and with the 1,3-dihydrofuro[3,4-b]quinoxaline 4,9-dioxide, and then it is incubated overnight at 37° C., under anaerobic conditions. On the next day, the test is read visually. The minimum inhibitory concentration (MIC) of test compound is the lowest concentration which prevents turbidity, i.e. which prevents growth of the microorganism. The antibacterial compounds of the invention are active against both gram-positive and gram-negative bacteria, and in particular they are active against *Streptococcus pyogenes*, *Escherichia coli*, *Salmonella choleraesuis*, *Pasteurella multocida* and *Treponema hyodysenteriae*. In vitro activities of certain of the compounds of the invention are shown in Table I.

In determining the in vivo activity of the compounds of the invention, the test compound is administered to mice which have been infected by intraperitoneal injection of a lethal inoculum of pathogenic bacteria. The test compound is administered using a multiple dosing regimen, using either the oral (PO) or the subcutaneous (SC) route. The inoculum of bacteria varies from one to about ten times the amount needed to kill 100% of the mice, under the conditions of the test. At the end of the test, the activity of a compound is assessed by counting the number of survivors among the treated animals, and expressing the activity of a compound as the percentage of animals which survive. In Table I, in vivo activities of several of the compounds of this invention against *Salmonella choleraesuis* and *Pasteurella multocida* are presented.

The in vitro antibacterial activity of the compounds of this invention makes them valuable as industrial antimicrobials, for example in water treatment, slime control, paint preservation and wood preservation, as well as for topical application as disinfectants. In the case of use of these compounds for topical application, it is often convenient to admix the active ingredient with a non-toxic carrier, such as vegetable or mineral oil or an emollient cream. Similarly, it can be dissolved or dispersed in liquid diluents or solvents such as water, alkanols, glycols or mixtures thereof. In most instances it is appropriate to employ concentrations of active ingredients of from about 0.1 percent to about 10 percent by weight, based on total composition.

growth and improves feed efficiency. Examples of animals which can be treated in this way are poultry (chickens, ducks, turkeys), cattle, sheep, dogs, cats, swine, rats, mice, horses, goats, mules, rabbits, mink, etc. The beneficial effects in growth rate and feed effi-

TABLE I

| Compound | MIC (mcg./ml.) | | | | | Percentage protection* | | | |
|---|---|---|---|---|---|---|---|---|---|
| | Strep. pyogenes | Esch. coli | Sal. choleraesuis | Past. multocida | Trep. hyodysenteriae | Sal. choleraesuis | | Past multocida | |
| | | | | | | SC | PO | SC | PO |
| 1-hydroxy-1-methyl-1,3-dihydrofuro[3,4-b]quinoxaline 4,9-dioxide | 0.78 | 1.56 | 1.56 | 12.5 | 0.09 | 100 | 100 | 100 | 100 |
| 1-methoxy-1-methyl-1,3-dihydrofuro[3,4-b]quinoxaline 4,9-dioxide | 0.78 | 3.12 | 1.56 | 3.12 | | 100 | 100 | 100 | 90 |
| 1-ethoxy-1-methyl-1,3-dihydrofuro[3,4-b]quinoxaline 4,9-dioxide | 3.12 | 12.5 | 12.5 | 12.5 | | 50 | 70 | | |
| 1-benzyloxy-1-methyl-1,3-dihydrofuro[3,4-b]quinoxaline 4,9-dioxide | 6.25 | 12.5 | 12.5 | 3.12 | | 60 | 40 | | |

*The dosage of test compound in the protection studies using *Salmonnella choleraesuis* was 25 mg./kg. of body weight, and using *Pasteurella multocida* it was 50 mg./kg. of body weight.

The in vivo antibacterial activity of the compounds of this invention makes them useful for the treatment of bacterial infections, due to susceptible organisms, in animals, particularly swine, cattle and poultry. Economically important diseases which can be controlled by the compounds of this invention are swine dysentery, swine plague, shipping and stockyard fever in cattle, fowl cholera, rabbit septicemia and scouring in vealer calves.

When used to control bacterial infections in animals, the compounds of this invention can be administered orally or parenterally, i.e. intramuscularly, subcutaneously or intraperitoneally, at a dosage of from about 1 mg./kg. of body weight to about 100 mg./kg. of body weight. However, in general, it will be found that a dosage in the range from about 5 mg./kg. of body weight to about 50 mg./kg. of body weight will suffice. The compounds can be administered alone, or they can be combined with various diluents and carriers, according to standard veterinary practice.

When parenteral use of a compound of this invention is contemplated, it can be combined with vehicles such as water, isotonic saline, isotonic dextrose, Ringer's solution, or non-aqueous diluents such as vegetable oils (cotton seed oil, sesame oil, corn oil) or dimethylsulfoxide. Buffering agents, local anesthetics and/or inorganic salts are commonly added to afford desirable pharacological properties.

In the case of oral use, a 1,3-dihydrofuro[3,4-b]quinoxaline 4,9-dioxide of this invention can be combined with various diluents including aqueous diluents, non-aqueous diluents and solid diluents, in the form of capsules, tablets, lozenges, troches, dry mixes, suspensions, solutions and dispersions.

'A particularly valuable application of the compounds of this invention is as animal growth promotants. The addition of a low level of one or more of the herein described 1,3-dihydrofuro[3,4-b]quinoxalines to the diet of healthy animals, both ruminant and non-ruminant, such that these animals receive the product over an extended period of time, at a concentration of from about 1 ppm to about 100 ppm., and usually from about 5 ppm. to about 50 ppm., blended with their feed, especially over a major portion of their active growth period, results in an acceleration of the rate of ciency are over and above what is normally obtained with complete nutritious diets containing all the nutrients, vitamins, minerals, and other factors known to be required for the maximum healthy growth of such animals. The animals thus attain market size sooner and on less feed. The 1,3-dihydrofuro[3,4-b]quinoxaline 4,9-dioxides can be blended with the animal's feed, or they can be administered in an equivalent amount via the animal's water ration.

The following Examples are provided solely for the purpose of illustration.

EXAMPLE I

1-Hydroxy-1-methyl-1,3-dihydrofuro[3,4-b]quinoxaline 4,9-dioxide

2-Acetyl-3-bromomethylquinoxaline 1,4-dioxide (72.0 g., 0.24 mol.) was added in three separate portions to boiling water (1,750 ml.) over a 1 hour period. Hydrogen bromide was evolved as the solvolysis proceeded, and upon continued refluxing for 3–4 hours all the starting material went into solution. The reaction mixture was cooled to room temperature and the resulting black precipitate was removed by suction filtration and discarded. The filtrate was neutralized to pH 6 with 25% sodium hydroxide solution, causing a dark brown precipitate to form. The precipitate was removed by suction filtration and discarded. The filtrate was then extracted with hot ethyl acetate (ten 150-ml. portions), and the combined extracts were dried over anhydrous magnesium sulfate and evaporated in vacuo.

This afforded 24.9 g. of crude product as tan crystals, m.p. 164°–166° C. The aqueous filtrate was then continuously extracted with methylene chloride, which give an additional 13.1 g. of crude product. The total crude product was, therefore, 40.0 g. (66% yield).

Analysis: — Calc'd for $C_{11}H_{10}N_2O_4$ (percent): C, 56.46; H, 4.31; N, 11.97. Found (percent): C, 56.19; H, 4.46; N, 12.09.

EXAMPLE II

1-Hydroxy-1-methyl-1,3-dihydrofuro[3,4-b]quinoxaline 4,9-Dioxide

2-Acetyl-3-acetoxymethylquinoxaline 1,4-dioxide (2.0 g., 7.24 mmol.) was dissolved in ice-cold concentrated hydrochloric acid (9 ml.). The reaction mixture was allowed to warm to room temperature and was stirred for 3 hours. Methylene chloride (20 ml.) was added, and the two-phase system was cooled in an ice-bath and made slightly basic (pH 8) with 50% sodium hydroxide solution. The methylene chloride layer was separated and the aqueous layer was extracted with more methylene chloride (two 20-ml. portions). The combined methylene chloride extracts were treated with activated carbon and evaporated under reduced pressure leaving a yellow solid. Recrystallization from methanol gave a 310 mg. (18% yield) of 1-hydroxy-1-methyl-1,3-dihydrofuro[3,4-b]quinoxaline 4,9-dioxide having m.p. 163°–165° C.

EXAMPLE III

The procedure of Example II is repeated, except that the quinoxaline starting material used therein is 2-acetyl-3-formyloxymethylquinoxaline 1,4-dioxide,
2-acetyl-3-propionyloxymethylquinoxaline 1,4-dioxide,
2-acetyl-3-butyryloxymethylquinoxaline 1,4-dioxide,
2-acetyl-3-isobutyryloxymethylquinoxaline 1,4-dioxide,
2-acetyl-3-n-valeroyloxymethylquinoxaline 1,4-dioxide and
2-acetyl-3-benzoylmethylquinoxaline 1,4-dioxide, respectively. This affords, in each case, 1-hydroxy-1-methyl-1,3-dihydrofuro[3,4-b]quinoxaline 4,9-dioxide.

EXAMPLE IV

1-Hydroxy-1-methyl-1,3-dihydrofuro[3,4-b]quinoxaline 4,9-Dioxide

A mixture of 0.578 g. (1.8 mmol.) of 2-acetyl-3-(2-tetrahydropyranyloxymethyl)quinoxaline 1,4-dioxide and 5.7 ml. of 40% aqueous acetic acid (prepared by mixing 40 parts of glacial acetic acid and 60 parts of water) was maintained at 40° C. for 3 hours. The solvents were removed by evaporation in vacuo. To the residue was added a small quantity of ethyl acetate, which was then removed by evaporation in vacuo. This procedure of adding ethyl acetate and then removing it by evaporation in vacuo was repeated several times. The residue was then washed with methyl isobutyl ketone, which finally afforded 0.354 g. (84% yield) of 1-hydroxy-1-methyl-1,3-dihydrofuro[3,4-b]quinoxaline 4,9-dioxide, m.p. 160°–162° C. (dec.).

EXAMPLE V

1-Methoxy-1-methyl-1,3-dihydrofuro[3,4-b]quinoxaline 4,9-Dioxide

A suspension of 30.0 g. (0.11 mol.) of 2-acetyl-3-acetoxymethylquinoxaline 1,4-dioxide in 300 ml. of methanol, saturated with dry hydrogen chloride, was stirred at ambient temperature for 2 days. The tan solid was collected by filtration, and then it was recrystallized from methanol, to give 17.0 g. (63% yield) of 1-methoxy-1-methyl-1,3-dihydrofuro[3,4-b]quinoxaline 4,9-dioxide, m.p. 201°–202° C.

Analysis: — Calcd. for $C_{12}H_{12}N_2O_4$ (percent): C, 58.12; H, 4.88; N, 11.30. Found (percent): C, 57.89; H, 4.78; N, 11.40.

EXAMPLE VI

Reaction of:
2-acetyl-3-acetoxymethylquinoxaline 1,4-dioxide,
2-acetyl-3-acetoxymethylquinoxaline 1,4-dioxide,
2-acetyl-3-acetoxymethylquinoxaline 1,4-dioxide,
2-acetyl-3-acetoxymethylquinoxaline 1,4-dioxide,
2-acetyl-3-acetoxymethylquinoxaline 1,4-dioxide,
2-acetyl-3-acetoxymethylquinoxaline 1,4-dioxide,
2-acetyl-3-formyloxymethylquinoxaline 1,4-dioxide
2-acetyl-3-propionyloxymethylquinoxaline 1,4-dioxide,
2-acetyl-3-butyryloxymethylquinoxaline 1,4-dioxide,
2-acetyl-3-isobutyryloxymethylquinoxaline 1,4-dioxide,
2-acetyl-3-n-valeroyloxymethylquinoxaline 1,4-dioxide and
2-acetyl-3-benzoyloxymethylquinoxaline 1,4-dioxide, respectively, with
ethanol,
propanol,
isopropanol,
1-butanol,
2-pentanol,
1-hexanol,
methanol,
ethanol,
methanol,
ethanol,
methanol and
ethanol, respectively, in the presence of hydrogen chloride, according to the procedure of Example V, affords the following compounds:

1-ethoxy-1-methyl-1,3-dihydrofuro[3,4-b]quinoxaline 4,9-dioxide,
1-propoxy-1-methyl-1,3-dihydrofuro[3,4-b]quinoxaline 4,9-dioxide,
1-isopropoxy-1-methyl-1,3-dihydrofuro[3,4-b]quinoxaline 4,9-dioxide,
1-butoxy-1-methyl-1,3-dihydrofuro[3,4-b]quinoxaline 4,9-dioxide,
1-(1-methylbutoxy)-1-methyl-1,3-dihydrofuro[3,4-b]quinoxaline 4,9-dioxide,
1-hexoxy-1-methyl-1,3-dihydrofuro[3,4-b]quinoxaline 4,9-dioxide,
1-methoxy-1-methyl-1,3-dihydrofuro[3,4-b]quinoxaline 4,9-dioxide,
1-ethoxy-1-methyl-1,3-dihydrofuro[3,4-b]quinoxaline 4,9-dioxide,
1-methoxy-1-methyl-1,3-dihydrofuro[3,4-b]quinoxaline 4,9-dioxide,
1-ethoxy-1-methyl-1,3-dihydrofuro[3,4-b]quinoxaline 4,9-dioxide,
1-methoxy-1-methyl-1,3-dihydrofuro[3,4-b]quinoxaline 4,9-dioxide and
1-ethoxy-1-methyl-1,3-dihydrofuro[3,4-b]quinoxaline 4,9-dioxide, respectively.

EXAMPLE VII

1-Ethoxy-1-methyl-1,3-dihydrofuro[3,4-b]quinoxaline 4,9-Dioxide

A suspension of 0.50 g. (2.13 mmol.) of 1-hydroxy-1-methyl-1,3-dihydrofuro[3,4-b]quinoxaline 4,9-dioxide in 10 ml. of ethanol containing 16 mg. of 4-toluenesulfonic acid monohydrate was stirred at 25° C. for 3 days. The tan solid was collected by filtration, and dried, to yield 0.37 g. (65% yield) of 1-ethoxy-1-methyl-1,3-dihydrofuro[3,4-b]quinoxaline 1,4-dioxide, m.p. 157°–159° C.

Analysis: — Calcd. for $C_{13}H_{14}N_2O_4$ (percent): C, 59.60; H, 5.39; N, 10.69. Found (percent): C, 59.27; H, 5.35; N, 10.82.

EXAMPLE VIII

1-Benzyloxy-1-methyl-1,3-dihydrofuro[3,4-b]quinoxaline 4,9-Dioxide

A suspension of 1.00 g. (4.26 mmol.) of 1-hydroxy-1-methyl-1,3-dihydro[3,4-b]quinoxaline 4,9-dioxide in 10 ml. of benzyl alcohol containing 32 mg. of 4-toluenesulfonic acid monohydrate was stirred at ambient temperature overnight. The solvent was then removed by evaporation in vacuo, leaving the crude product as an oil which solidified on trituration using ethyl acetate-hexane. Recrystallization from ethyl acetate-hexane then afforded 0.28 g. (21% yield) of 1-benzyloxy-1-methyl-1,3-dihydrofuro[3,4-b]quinoxaline 4,9-dioxide, m.p. 112°–116° C.

EXAMPLE IX

Reaction of 1-hydroxy-1-methyl-1,3-dihydrofuro[3,4-b]quinoxaline 4,9-dioxide with the appropriate alkanol, according to the procedure of Example VII, produces the following compounds:

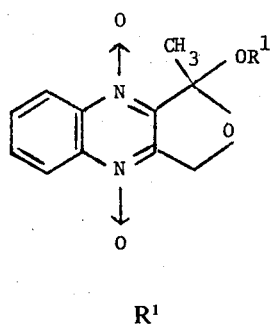

$R^1$ $CH_3$
$CH_3CH_2CH_2$
$CH_3(CH_2)_2CH_2$
$(CH_3)_2CH\ CH_2$
$CH_3(CH_2)_3CH_2$
$CH_3(CH_2)_4CH_2$

EXAMPLE X

1-Hydroxy-1-methyl-1,3-dihydrofuro[3,4-b]quinoxaline 4,9-Dioxide

To a mixture of 1,500 ml. of acetone and 75 ml. of water, containing 3.78 g. (0.02 mol.) of 4-toluenesulfonic acid monohydrate, was added 63.6 g. (0.26 mol.) of 1-methoxy-1-methyl-1,3-dihydrofuro[3,4-b]quinoxaline 4,9-dioxide. The reaction mixture was heated under reflux for 4.5 hours and then allowed to cool to ambient temperature. The solvent was removed by evaporation in vacuo, and the residue was washed with ether. This afforded 58.7 g. (98% yield) of crude product. The crude product was recrystallized from water with the aid of activated carbon, to give a 68% yield of product having m.p. 159°–160° C.

EXAMPLE XI

Hydrolysis of each of the furoquinoxaline compounds produced in Examples VI, VII, VIII and IX, according to the procedure of Example X, produces, in each case, 1-hydroxy-1-methyl-1,3-dihydrofuro[3,4-b]quinoxaline 4,9-dioxide.

PREPARATION A

2-Acetyl-3-bromomethylquinoxaline 1,4-Dioxide

To a stirred suspension of 343 g. (1.57 mol.) of 2-acetyl-3-methylquinoxaline 1,4-dioxide in 3,000 ml. of methanol was added (1.74 mole) of bromine over a period of 2 hours. The reaction mixture was then stirred for 5 days at room temperature. The resulting yellow solid was collected by suction filtration, washed with methanol and ether, and dried to give 331 g. (71% yield) of 2-acetyl-3-bromomethylquinoxaline 1,4-dioxide, m.p. 164°–166° C.

PREPARATION B

2-Acetyl-3-acetoxymethylquinoxaline 1,4-Dioxide

To a stirred slurry of 50.0 g. (0.168 mol.) of 2-acetyl-3-bromomethylquinoxaline 1,4dioxide in 200 ml. of N,N-dimethylformamide, was added 18.2 g. (0.185 mol.) of potassium acetate, followed by 4.15 g. (0.025 mol.) of finely ground potassium iodide. Stirring was continued for 20 minutes at ambient temperature, and then the reaction mixture was filtered. The dark filtrate was added dropwise to 4,000 ml. of ether, and the solid which precipitated was removed by filtration and discarded. Evaporation of the ether in vacuo afforded a yellow solid which was recrystallized from methanol. This gave 31.6 g. (76% yield) of 2-acetyl-3-acetoxymethylquinoxaline 1,4-dioxide having m.p. 124°–125° C.

Analysis: Calc'd. for $C_{13}H_{12}N_2O_5$ (percent): C, 56.57; H, 4.38; N, 10.15. Found (percent): C, 56.83; H, 4.31; N, 10.37.

PREPARATION C

Reaction of 2-acetyl-3-bromomethylquinoxaline 1,4-dioxide with the potassium salt of the appropriate carboxylic acid, according to the procedure of Preparation B, produces the following compounds:

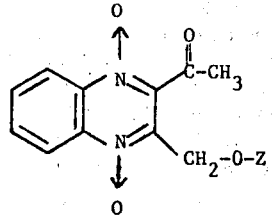

Z

CO—H
CO—$CH_2CH_3$
CO—$CH_2CH_2CH_3$
CO—$CH_2(CH_3)_3$
CO—$CH_2(CH_2)_2CH_3$
CO—$C_6H_5$

PREPARATION D 1-(2-Tetrahydropyranyloxy)-2,4-pentanedione (A) Ethyl 2-(2-tetrahydropyranyloxy)acetate.

To a stirred solution of 15.5 g. (0.15 mol.) of ethyl glycolate in 60 ml. of methylene chloride, cooled to 5° C., was added 12.6 g. (0.15 mol.) of dihydropyran, followed by 50 mg. of 4-toluenesulfonic acid monohydrate. After the immediate exothermic reaction which ensued had subsided, the methylene chloride solution was washed successively with water, 5% sodium bicarbonate and water. The dried solution was then evaporated to give 23.8 g. (85% yield) of ethyl 2-(2-tetrahydropyranyloxy)acetate as a clear oil.

(B) 1-(2-tetrahydropyranyloxy)-2,4-pentanedione.

Under an atmosphere of dry nitrogen, 2.35 g. of a 50% dispersion of sodium hydride in mineral oil was washed several times with hexane. To the oil-free sodium hydride was then added 25 ml. of ether, followed by 9.18 g. of ethyl 2-(2-tetrahydropyranyloxy)acetate, followed by 3.96 ml. of acetone dissolved in a 10 ml. of ether. The reaction mixture was stirred at ambient temperature for 1.5 hours, at which point a vigorous, exothermic reaction took place. After the exothermic reaction had subsided, the reaction mixture was stirred for an additional 30 minutes and then it was quenched by pouring it into an ice-cold mixture prepared from 49 ml. of 11N hydrochloric acid and 100 ml. of water. After 5 minutes, the organic phase was separated, washed with water, dried and evaporated to give 7.8 g. of an oil. This oil was distilled, to give 4.5 g. (46% yield) of 1-(2-tetrahydropyranyloxy)-2,4-pentanedione as a clear liquid, b.p. ca. 60° C. (0.4 mm).

PREPARATION E

2-Acetyl-3-(2-tetrahydropyranyloxymethyl)quinoxaline 1,4-Dioxide

To a solution of 0.5 g. (3.67 mmol.) of benzofurazan 1-oxide in 25 ml. of dry ethanol was added 16 mg. of powdered sodium hydroxide. The reaction mixture was stirred at ambient temperature for 18 hours, and then the solvent was removed by evaporation in vacuo. The residue was triturated with ether. A small amount of insoluble material was removed by filtration, and then the ether was evaporated in vacuo. This left an oil which solidified on the addition of ethyl acetate-hexane. The solid was collected by filtration and dried, to yield 0.247 g. (21% yield) of 2-acetyl-3-(2-tetrahydropyranyloxymethyl)quinoxaline 1,4-dioxide.

What is claimed is:

1. A compound of the formula

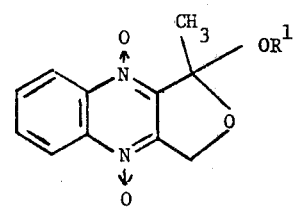

wherein $R^1$ is selected from the group consisting of hydrogen, alkyl having from one to six carbon atoms and benzyl.

2. The compound according to claim 1, wherein $R^1$ is hydrogen.

3. The compound according to claim 1, wherein $R^1$ is methyl.